US011517221B2

(12) United States Patent
Hollingsworth et al.

(10) Patent No.: US 11,517,221 B2
(45) Date of Patent: Dec. 6, 2022

(54) INDICATOR PANELS FOR INCONTINENCE PRODUCTS

(71) Applicants: NEW YORK UNIVERSITY, New York, NY (US); PIXIE SCIENTIFIC, LLC, New York, NY (US)

(72) Inventors: Andrew D. Hollingsworth, Princeton, NJ (US); Scott Meek, Watchung, NJ (US); William Gotimer, Ridgewood, NY (US)

(73) Assignees: New York University, New York, NY (US); Pixie Scientific TTC, New York, NY (US)

( * ) Notice: Subject to any disclaimer, the term of this patent is extended or adjusted under 35 U.S.C. 154(b) by 1101 days.

(21) Appl. No.: 16/074,735

(22) PCT Filed: Feb. 1, 2017

(86) PCT No.: PCT/IB2017/050548
§ 371 (c)(1),
(2) Date: Aug. 1, 2018

(87) PCT Pub. No.: WO2017/134584
PCT Pub. Date: Aug. 10, 2017

(65) Prior Publication Data
US 2021/0177351 A1     Jun. 17, 2021

Related U.S. Application Data

(60) Provisional application No. 62/290,280, filed on Feb. 2, 2016.

(51) Int. Cl.
*A61F 13/42* (2006.01)
*A61B 5/145* (2006.01)
(Continued)

(52) U.S. Cl.
CPC ...... *A61B 5/14507* (2013.01); *A61B 5/14539* (2013.01); *A61B 5/14546* (2013.01);
(Continued)

(58) Field of Classification Search
CPC ............... A61F 13/42; A61F 2013/422; A61F 2013/427; A61F 2013/8473; A61L 15/56;
(Continued)

(56) References Cited

U.S. PATENT DOCUMENTS 5,181,905 A * 1/1993 Flam ................... A61L 15/56
374/161
6,515,194 B2 * 2/2003 Neading .................. A61F 13/42
604/361
(Continued)

OTHER PUBLICATIONS

International Search Report and Written Opinion in PCT/IB2017/050548, dated May 24, 2017, 10 pages.

*Primary Examiner* — Catharine L Anderson
(74) *Attorney, Agent, or Firm* — Foley & Lardner LLP

(57) ABSTRACT

The present disclosure is directed to indicating systems and methods for incontinence products. The indicating system may include an indicator panel for an incontinence product that is adapted to provide a qualitative or quantitative indication of a characteristic of a liquid absorbed by the indicator panel.

16 Claims, 1 Drawing Sheet

(51) Int. Cl.
  *A61B 5/20*   (2006.01)
  *A61B 5/00*   (2006.01)
  *A61L 15/24*  (2006.01)
  *A61L 15/60*  (2006.01)
  *A61B 10/00*  (2006.01)
  *A61F 13/84*  (2006.01)

(52) U.S. Cl.
  CPC ............ *A61B 5/207* (2013.01); *A61B 5/6808* (2013.01); *A61F 13/42* (2013.01); *A61L 15/24* (2013.01); *A61L 15/60* (2013.01); *A61B 10/007* (2013.01); *A61B 2010/0006* (2013.01); *A61F 2013/422* (2013.01); *A61F 2013/427* (2013.01); *A61F 2013/8473* (2013.01)

(58) Field of Classification Search
  CPC . A61B 5/14507; A61B 5/14539; A61B 5/207; A61B 5/6808
  See application file for complete search history.

(56) References Cited

U.S. PATENT DOCUMENTS

| | | | |
|---|---|---|---|
| 9,131,893 B2* | 9/2015 | Faybishenko | A61F 13/15699 |
| 9,486,368 B2* | 11/2016 | Nelson | A61F 13/15739 |
| 10,383,564 B2* | 8/2019 | Meek | A61B 5/14507 |
| 2008/0306461 A1 | 12/2008 | Jan | |
| 2009/0157024 A1 | 6/2009 | Song | |
| 2009/0275908 A1 | 11/2009 | Song | |

* cited by examiner

INDICATOR PANELS FOR INCONTINENCE PRODUCTS

BACKGROUND

A variety of ailments and disorders may be detected and/or diagnosed by analysis of a subject's urine sample. For example, the content of a urine sample potentially carries evidence of developing under-hydration or infection, or of endocrine or metabolic system problems. Unfortunately, urine analysis is typically performed in a clinical or laboratory setting, and therefore requires both time and expense.

Existing diagnostic tools for monitoring a specified characteristic of the urine may include colorimetric test strips. Such test strips typically include appropriate detection reagents that are, or are coupled with, colorimetric dyes. However, the colors of such dyes typically shift upon drying, and/or are intrinsically unstable. As a result, the initial color of the test strip may fade after the initial test is completed.

What is needed is a colorimetric indicator system for testing one or more characteristics of a urine sample that is capable of producing an indicative color change that is both distinctive and stable over time In particular, the availability of a stable colorimetric indicator system would permit urine testing to move beyond the necessity of collecting a urine sample, with its attendant inconvenience and potential for contamination, improper handling, and/or spilling the sample, and the necessity of immediate reading or interpretation of the colorimetric response.

Embodiments of the colorimetric test systems and methods of the present disclosure may enable the detection of potential health concerns by permitting the testing of a subject's urine through the routine use of an incontinence product that incorporates the colorimetric test system.

SUMMARY

One embodiment relates to an indicating panel for an incontinence product. The indicating patent comprises a porous sheet. The porous sheet is impregnated with a first indicator that is selected to respond to a target analyte by creating a detectable response and a polymeric mordant that is selected to stabilize indicators that generate detectable responses, wherein the polymeric mordant has been stabilized with respect to both basic and thermal degradation.

Another embodiment relates to an indicating incontinence product. The indicating incontinence product comprises an absorbent core and a porous inner sheet. The porous inner sheet is adjacent to the absorbent core. The porous inner sheet is impregnated with a first indicator, a second indicator, and a polymeric mordant. The first indicator is selected to respond to a target analyte by creating a detectable response. The second indicator is selected to respond to the detectable response of the first indicator by generating a second detectable response. The polymeric mordant is selected to stabilize indicators that generate detectable responses, and has been stabilized with respect to basic degradation, thermal degradation, and cross-reactivity with the first indicator.

DETAILED DESCRIPTION

The present disclosure is directed to indicating systems and methods for generating detectible responses from an indicator, for example for use with incontinence products. The indicating system may include an indicator panel for an incontinence product that is adapted to provide a qualitative or quantitative indication of a characteristic of a liquid absorbed by the indicator panel.

Embodiments of Indicating Systems

Figure 1:
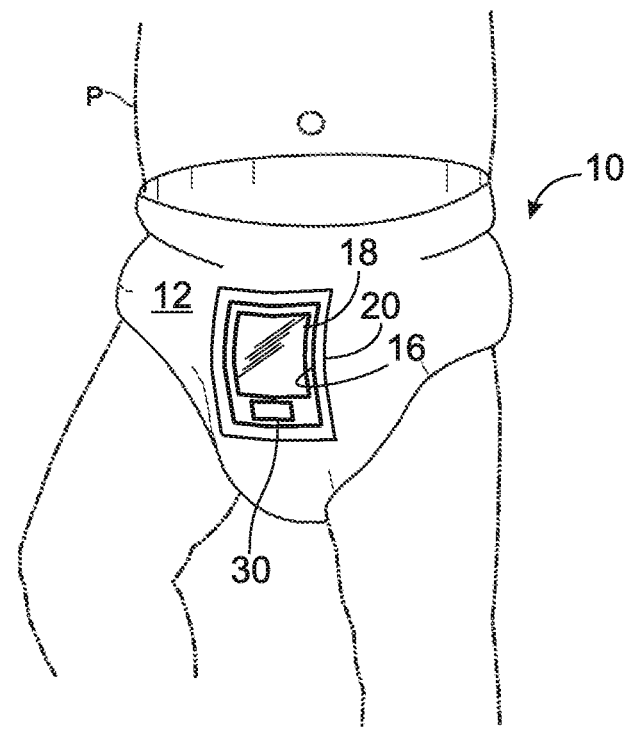
FIG. 1 depicts an embodiment of an incontinence product according to an embodiment of the present disclosure.

FIG. 1 depicts an illustrative incontinence product 10 worn by a patient P according to selected aspects of the present disclosure. Incontinence product 10 is depicted as a diaper, but it should be appreciated that the embodiments of the present disclosure may confer benefits and advantageous properties on any of a variety of incontinence products, including, among others, diapers for a human infant, toddler, child, or adult or a pet animal, or incontinence pads which may be inserted into a patient's underwear. It should be appreciated that the title of patient is intended to include all suitable subjects (e.g., humans, animals, etc.) and is thus not limited to hospital use or use by medical professionals.

Figure 2:
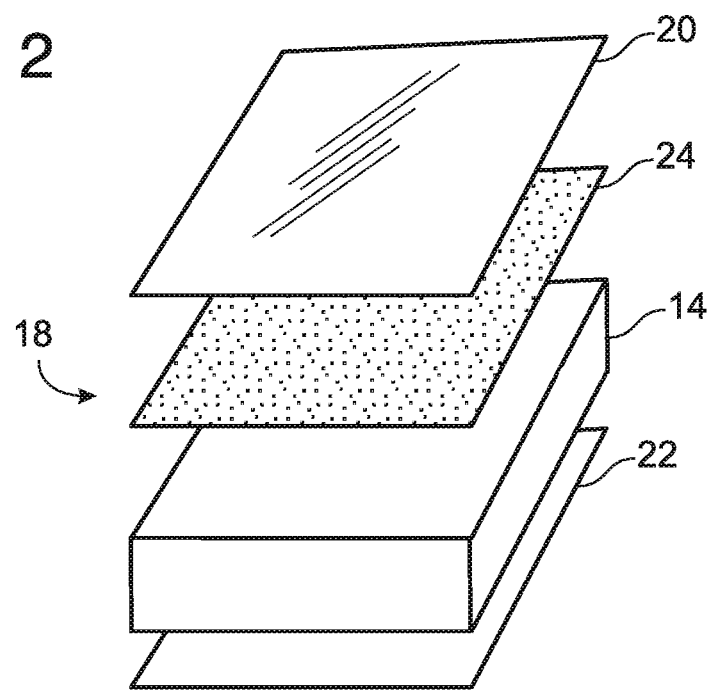
FIG. 2 is a partially exploded sectional view of the incontinence product of FIG. 1.

Diaper 10 of FIG. 1 may be disposable or reusable either partially or totally, and may include an outermost layer 12. The outermost layer may be coupled to an absorbent core 14, as shown in FIG. 2), where the absorbent core 14 may include a superabsorbant polymer, such as sodium polyacrylate polymer, that is capable of absorbing up to several hundred times its mass in water. Diaper 10 and may include a cut-out 16 in the top layer 12 to accommodate an indicator panel 18. Indicator panel 18 may be disposed in cut-out 16 and thereby in contact with absorbent core 14. In one embodiment of the present disclosure, transparent tape 20 may be disposed over indicator panel 18 and a portion of waterproof layer 12 to seal cut-out 16.

Transparent tape 20 may be transparent waterproof film, such as OPSITE® FLEXIFIX® Transparent Film, disposed over indicator panel 18 to provide a sufficient seal and/or to allow indicator panel 18 to be properly viewed, which may allow a user to easily view the indicator panel without removing diaper 10 from its wearer.

Diaper 10 may include any suitable configuration of diaper layers and components for collecting a sample, such as urine, providing for patient comfort, providing for convenience of use and/or viewing the indicator panel 18. An optional privacy cover layer (not shown) may be removably attached and configured to diaper 10 so that diaper 10 has an appearance of a regular diaper, which may be desirable for maintaining confidentiality.

FIG. 2 depicts a partially exploded cross-sectional view of a portion of diaper 10. As shown, diaper 10 may include a permeable innermost layer 22, absorbent core 14, and top layer 12 which may include one or more layers and may be waterproof. Innermost layer 22 may be in contact with a crotch region of the wearer when diaper 10 is being worn. A urine sample produced by the patient may contact innermost layer 22, travel through absorbent core 14, and then contact and/or permeate indicator panel 18.

FIG. 2 additionally depicts an exploded cross-sectional view of indicator panel 18, which may include a porous inner sheet 24 that is adjacent to and in contact with the absorbent core 14. Inner sheet 24 includes an indicator configured to generate a detectable response when contacting by a material, such as a liquid, exhibiting a target analyte.

A target analyte may be the presence or concentration of any component of a patient's sample that may be indicative of, or correlated with, the patient's health or well-being. For example, in one aspect of the present disclosure the detection of a particular marker characteristic in a sample may be indicative of a specific health condition, ailment, or injury. The target analyte may be the presence of one or more substances in the sample that are not generally present, or the target analyte may be a substance in concentration or range of concentrations that correlate with a health condition. For example, the presence of dissolved salts in a urine sample is normal, but an elevated concentration of those same salts may indicate dehydration or other health issue.

The indicator may be selected to respond to the target analyte by creating a detectable response. A detectable response, as used herein, is a change in a property of the indicator that is capable of being perceived, either by direct visual observation or instrumentally, preferably by direct visual observation. The detectable response may be colorimetric (color-changing) or luminescent (such as fluorescent), and may be the appearance or disappearance of color, or a shift in absorbance wavelength or, in the case of fluorescence, a shift in emission wavelength. In one aspect of the present disclosure, the detectable response is a color change, and preferably a change from substantially colorless to highly colored.

It may be advantageous to utilize an indicator that is at least somewhat selective for the target analyte, that is, an indicator that generates comparatively few false positives. For example, the indicator may be selective for a target analyte that is an ion, such as Cl−, Na+, K+, Ca2+, Mg2+, Zn2+, among others. Alternatively, the indicator may be selected for a target analyte that is H3O+, i.e., sample pH.

A number of polydentate chelating moieties (or complex-ones) may exhibit specificity for complexing particular ions. These ion-sequestering moieties may include amine binding groups or carboxylic acid binding groups, and may include without limitation ethylenediamine, ethylenediaminetetraacetic acid (EDTA), 1,2-bis(o-aminophenoxy)ethane-N,N,N',N'-tetraacetic acid (BAPTA), aminophenoltriacetic acid (APTRA), crown ethers, etc. Once a suitable chromophore or fluorophore reporter molecule is bound to such a chelating moiety, the spectral properties of the reporter may detectably change upon the binding of the target ion. A variety of such indicators and their structures may be found in The Molecular Probes Handbook 11th Edition, 2010, hereby incorporated by reference.

In one aspect of the present disclosure, inner sheet 24 may include a pair of coupled indicators, where the first indicator may be selected to identify the target analyte by creating a reporting condition that is measurably distinct from the condition of the inner sheet prior to exposure to the sample, or measurably distinct from the condition of the first indicator before contact with a control sample. The second indicator of the coupled pair may be selected to generate a detectable response when the first indicator creates a reporting condition. For example, the reporting condition may be a change in pH, and the second indicator may generate a change in color in response to the change in pH.

Where the indicator panel includes a pair of coupled indicators, the indicators are screened to insure that they are compatible, and that the desired characteristic(s) of the patient sample can be determined. For example, the indicator poly(methyl vinyl ether-alt-maleic acid) (PMVEMA) couples effectively with colorimetric indicators such as bromothymol blue (BTB), pKa=7.3: Hln (acid form, yellow)+H2O↔In− (base form, blue)+H3O+, where In=indicator, Ka=acid dissociation constant. Other colorimetric indicators include bromocresol purple (pKa=6.3), phenol red (pKa=8.0), and neutral red (pKa=6.7). Note that the protonated form of methyl red, a leuco dye, is positively charged. The binding of dye molecules with polymeric buffer and/or mordant is expected to shift the pKa slightly.

Accordingly, one or more of the indicator components of the indicator panel may be titrated to determine whether the useful detection range of that indicator will offer a suitably distinct color change under the expected sample conditions.

Inner sheet 24 may additionally incorporate a polymeric mordant that is selected to stabilize an indicator that is exhibiting a detectable response. The polymeric mordant may be selected to immobilize the indicator, or otherwise prevent the detectable response from reverting or fading over time. In one embodiment, the polymeric mordant is designed to immobilize the chromogenic indicator mentioned above. Its purpose is to prevent problems associated with color deterioration over one or more hours, which would change the reading accuracy of the test sensor. Structurally, it is a copolymer comprised of a quaternary alkyl ammonium compound and a water insoluble acrylate. In one implementation, the minority monomer can be (3-acrylamidopropyl)trimethyl ammonium chloride, while the majority monomer is 85-97 mol % organic, typically methyl acrylate. This class of material is called an ion-sensitive, water dispersible cationic polymer. A controlled concentration of salt in the wetting solution insolubilizes the otherwise water-soluble polymer; conversely, the dilution of the salt solution with additional water releases the intramolecular binding. The so-called "trigger property" of the polymer is not relevant to usage in the mordant to the extent that mordant-coated substrates will not be exposed to water with less than 0.3% w/w salt. Thus, the mordant will always remain physically attached to the test panel. Furthermore, the cationic nature of the mordant will form a complex with oppositely charged molecules such as bromothymol blue (BTB), thereby protecting the colored reaction product for a desired period of time. The polymeric mordant may be prepared according to a variety of polymerization methods, desirably a solution polymerization method. An azo compound is used to initiate the free radical addition polymerization. The mordant, in solid form, is a tough, expanded closed-celled foam, which is soluble in water, acetone, and water-alcohol mixtures. In this way, the examination of inner sheet 24 provides an accurate and stable result that reflects the presence or absence of the target analyte in the sample. The polymeric mordant of inner sheet 24 has typically been stabilized with respect to basic, i.e., >pH 7, degradation, thermal degradation, and cross-reactivity with the first indicator.

In one embodiment, the mordant is incorporated, such as into the inner sheet generally as follows: Solutions of 5-10 wt % mordant in water/ethanol; 9-10 wt % PMVEMA and 5-5.5 wt % KOH in water, and 5-10 mg/mL BTB in water/ethanol are prepared. Polyoxyethylene sorbitan monolaurate surfactant (Tween 20) is added to both the buffer and mordant solutions at 2 wt %. Tween 20 enhances proton exchange via hydrogen bonding. Chromatography paper is sequentially soaked in the mordant, buffer, dye solutions, or mixtures thereof, with 60-80° C. drying between steps. The paper is cut into squares for testing with KCl or NaCl solutions ranging in specific gravity from 1.005 to 1.035.

Scanning electron microscopy images of the mordant-infused paper show that the polymer appears to cover the cellulosic fibers completely.

The polymeric mordant may be a polymer that is derivatized by both hydrophilic and hydrophobic functional groups, such as a polymeric cationic surfactant. In a more specific aspect, the polymeric mordant includes poly[methyl acrylate-co-(3-acrylamidopropyl)trimethyl ammonium chloride]. The polymeric mordant may be selected to be capable of binding or immobilizing the first indicator and second indicator (when present).

Where the polymeric mordant is derivatized by quaternary ammonium functional groups, the polymeric mordant may be stabilized by replacing those protons positioned beta to the quaternary ammonium group with lower alkyls having 1-6 carbons (see Scheme 1 below). In this way, the functional group is no longer susceptible to the Hofmann Elimination reaction (see Scheme 2 below), and the polymeric mordant is thereby stabilized with respect to both basic and thermal degradation.

Scheme 1

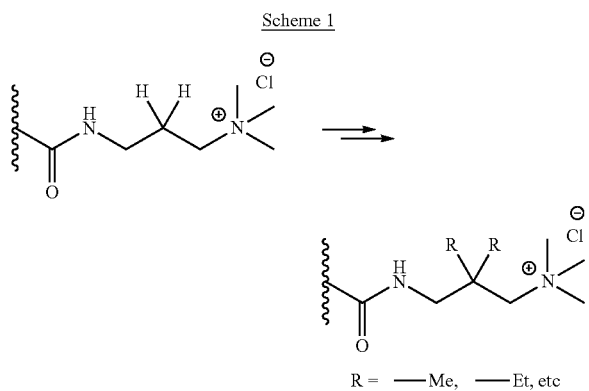

Scheme 2

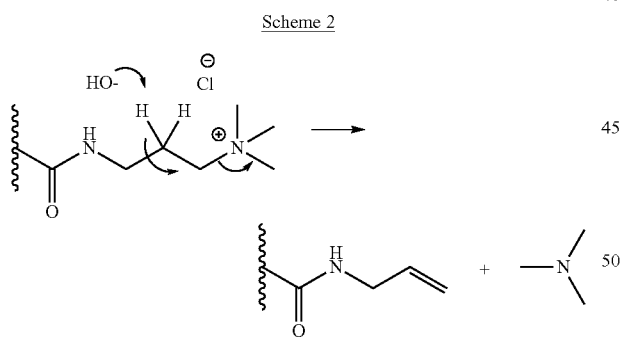

Inner sheet 24 may be selected from any appropriately hydrophilic, absorbent, and/or porous material. The composition of the inner sheet is selected to be substantially chemically and biologically inert with respect to biological fluids and the typical components present therein. In one aspect of the present disclosure, the inner sheet is formed from a polymeric fiber, silica gel, or alumina pad. Where the inner sheet includes polymeric fiber, it may be cellulosic fiber.

The indicator panel 18 may be configured, and the coupled indicators selected, so that a desired and suitably distinct color change occurs in the presence of the target analyte. The color change may be selected so that a simple visual inspection will reveal a positive diagnostic response. Alternatively, or in addition, it may be advantageous to inspect the indicator panel 18 using a data acquisition device, such as a camera or optical scanner, that is coupled directly or indirectly with a processor configured to process and/or analyze the acquired data.

For example, the data acquisition device may include a smartphone camera, and the processor may be the smartphone processor executing an application that is configured to analyze the acquired diagnostic data. Alternatively, or in addition, the data acquisition device may be directly or indirectly coupled to remote server via an online service (or network). Suitable data acquisition and transmission devices have been described in copending U.S. patent application Ser. No. 14/065,360 to Faybishenko, hereby incorporated by reference for all purposes.

Possible Advantages of Embodiments of the Invention

By creating diapers or pads with attached indicating panels, the necessity of dipping urine analysis strips into a cup with urine is eliminated. In one aspect of the present disclosure, the indicating panel is configured so that a detectable color change at the indicator panel corresponds to a potentially negative result, so that the appearance of color on an outer surface of the diaper provides an attention-getting signal as to the patient's condition. The detectable color change of the present indicator panels is additionally stable over time, so that even if the test result is not observed immediately, the test result remains valid.

The present indicating panels are ideally suited for incorporation into incontinence products, such as disposal diapers and pads, that are used regularly or routinely, as they provide an unobtrusive and nonintrusive means of monitoring one or more patients without the necessity of requiring them to undergo a testing procedure or collecting a specific sample, while the color stability of the present indicating panels permit the test result to be obtained at a time that is convenient for the care-giver, for example, when the incontinence product would normally be changed.

By using one such diaper, a caregiver may understand over a period of time whether a child or other patient is becoming dehydrated, for example, or developing any of a variety of other illnesses. This utility may be particularly advantageous in nurseries, child-care facilities, long-term care facilities, and even in the home.

Selected Embodiments of Indicator Panels

The following examples of indicators and indicator systems are intended to set out various operational principles and preferred embodiments, and should not be considered to limit the scope of the present disclosure. It will be apparent to those skilled in the art that various changes in form and detail may be made to these examples without departing from the spirit and scope of the disclosure.

Example 1. Indicator Panel for Specific Gravity

An adult urine sample may typically have a specific gravity in the range of 1.000 to 1.030, and observation of an increase in urine specific gravity may reflect a number of health issues, including for example dehydration, diarrhea, emesis, UTI, aglucosuria, and renal artery stenosis, among many others. A urine specific gravity greater than 1.035 is consistent with serious dehydration.

An indicator panel configured to detect high specific gravity is constructed by impregnating an inner sheet with a first indicator and second indicator. The first indicator is poly(methyl vinyl ether-alt-maleic acid) (PMVEMA), a polymer that responds to increased salt concentrations by lowering local pH. The PMVEMA polymer is titrated to the desired pH level before use. The second indicator is a pH indicator that is bromothymol blue (BTB) or a related dye, and the inner sheet is impregnated with the BTB indicator to a concentration of 1-2 wt %, and impregnated with the titrated PMVEMA to a concentration of 5-12 wt %.

The inner sheet is also impregnated with a stabilized polymeric mordant for example to a concentration of 5-12 wt %.

While the specific gravity of urine may be due to the presence of proteins or other components other than ion content, measured values of ionic strength can be correlated with specific gravity. When a urine sample passes through the absorbent core and into the inner sheet, the titrated PMVEMA changes the local pH in response to the ionic strength of the urine sample. The pH indicator bromothymol blue then changes color in response to the pH change, and the polymeric mordant immobilizes the indicator.

The color of the indicator on the outer surface of the indicator panel indicates that the urine sample exhibits a high specific gravity.

It should be appreciated that the specific components of the disclosed indicator panels may be selected so that the indicator panel, and the incontinence product it may be attached to, is useful for any of a number of target analytes. For example, indicator panels may be prepared to detect and/or quantify the presence of creatinine, magnesium ions, ketones, and L-dopa, among others.

What is claimed is:

1. An indicating panel for an incontinence product, comprising:
   a permeable inner layer;
   an absorbent core adjacent the permeable inner layer;
   a porous sheet adjacent to the absorbent core and in fluid communication with the permeable inner layer therethrough, the porous sheet impregnated with:
      a first indicator that is selected to respond to a target analyte by creating a first indicator detectable response; and
      a polymeric mordant that is selected to stabilize a second indicator that generates a second indicator detectable response, wherein the polymeric mordant has been stabilized with respect to both basic and thermal degradation.

2. The indicating panel of claim 1, wherein the polymeric mordant has been stabilized with respect to cross-reactivity with the first indicator.

3. The indicating panel of claim 1, wherein the first indicator is a colorimetric indicator.

4. The indicating panel of claim 1, wherein the second indicator is selected to respond to the detectable response of the first indicator by generating a second detectable response.

5. The indicating panel of claim 4, wherein the second indicator is a colorimetric indicator.

6. The indicating panel of claim 4, wherein at least one of the first indicator and second indicator is a pH indicator.

7. The indicating panel of claim 4, wherein at least one of the first indicator and second indicator is a metal ion indicator.

8. The indicating panel of claim 1, wherein the first indicator is poly(methyl vinyl ether-alt-maleic acid) (PMVEMA).

9. The indicating panel of claim 8, wherein the second indicator is a pH indicator.

10. The indicating panel of claim 1, wherein the polymeric mordant is derivatized by a plurality of quaternary ammonium functional groups; and wherein each proton beta to each quaternary ammonium functional group is replaced by a lower alkyl having 1-6 carbons.

11. The indicating panel of claim 1, wherein the polymeric mordant comprises a quaternary alkyl ammonium compound and water insoluble acrylate compound, the polymeric mordant.

12. An indicating incontinence product, comprising:
    a permeable inner layer;
    an absorbent core adjacent the permeable inner layer;
    a porous inner sheet, adjacent to the absorbent core, that is impregnated with a first indicator, a second indicator, and a polymeric mordant, wherein:
       the first indicator is selected to respond to a target analyte by creating a detectable response;
       the second indicator is selected to respond to the detectable response of the first indicator by generating a second detectable response; and
       the polymeric mordant is selected to stabilize indicators that generate detectable responses, and has been stabilized with respect to basic degradation, thermal degradation, and cross-reactivity with the first indicator; and
    an impermeable layer adjacent the porous inner sheet, wherein the porous inner sheet is disposed between the absorbant core and the impermeable layer.

13. The incontinence product of claim 12, wherein the absorbent core includes a superabsorbent polymer.

14. The incontinence product of claim 12, wherein the absorbent core includes a superabsorbent sodium polyacrylate polymer.

15. The incontinence product of claim 12, wherein
    the polymeric mordant is selected to irreversibly stabilize the second indicator that is generating the detectable response.

16. The incontinence product of claim 12, wherein the polymeric mordant comprises a quaternary alkyl ammonium compound and water insoluble acrylate compound.

* * * * *